United States Patent
Salzer et al.

(10) Patent No.: US 12,210,007 B2
(45) Date of Patent: Jan. 28, 2025

(54) ELECTROCHEMICAL CELL STIRRING

(71) Applicant: Hach Company, Loveland, CO (US)

(72) Inventors: Corey Alan Salzer, Fort Collins, CO (US); Dan Jonathan Kroll, Fort Collins, CO (US)

(73) Assignee: Hach Company, Loveland, CO (US)

( * ) Notice: Subject to any disclaimer, the term of this patent is extended or adjusted under 35 U.S.C. 154(b) by 342 days.

(21) Appl. No.: 17/894,803

(22) Filed: Aug. 24, 2022

(65) Prior Publication Data

US 2024/0069002 A1 Feb. 29, 2024

(51) Int. Cl.
 *G01N 33/18* (2006.01)
 *G01N 1/38* (2006.01)
 *G01N 27/42* (2006.01)

(52) U.S. Cl.
 CPC ......... *G01N 33/1853* (2013.01); *G01N 1/38* (2013.01); *G01N 27/423* (2013.01)

(58) Field of Classification Search
 CPC .... G01N 31/164; G01N 1/38; G01N 33/1853; G01N 27/44; G01N 27/423
 See application file for complete search history.

(56) References Cited

U.S. PATENT DOCUMENTS 6,463,225 B1 * 10/2002 Abe .................. G03G 15/0865
399/61

FOREIGN PATENT DOCUMENTS

CN 102826634 A * 12/2012
CN 205893025 U * 1/2017

* cited by examiner

*Primary Examiner* — Paul M. West
(74) *Attorney, Agent, or Firm* — FERENCE & ASSOCIATES LLC

(57) ABSTRACT

An embodiment provides a method for stirring a sample in a cell, including: providing a cell comprising a sample chamber; placing a boron-doped diamond electrode on an inner surface of the sample chamber, placing a removable stir bar in the sample chamber, the removable stir bar directly contacting and touching the boron-doped diamond electrode; and wherein the stir bar can be operated to rotate within the sample chamber upon the boron-doped diamond electrode. Other aspects are described and claimed.

20 Claims, 2 Drawing Sheets

ELECTROCHEMICAL CELL STIRRING

FIELD

This application relates generally to water quality measurement, and, more particularly, to stirring during measurement of alkalinity in a sample.

BACKGROUND

Ensuring water quality is critical in a variety of industries such as pharmaceuticals, food and beverage, and other manufacturing fields. Additionally, ensuring water quality is critical to the health and well-being of humans, animals, and plants which are reliant on water for survival as well as the overall health of the environment. One attribute of water that may be measured is the alkalinity. Measurement of alkalinity may allow for identification of buffering capacity of the water, which is crucial in understanding the amount of acid or base that can be added to the water before a significant change in pH occurs. It may also allow computation of other important characteristics for ensuring water quality, such as corrosivity. One method to test for alkalinity includes a complex titration process which requires a chemical titrant to be added to the sample in a carefully measured manner. This method requires accurate measurement and a significant time duration to perform the analysis of alkalinity.

BRIEF SUMMARY

In summary, one embodiment provides a method for stirring a sample in a cell, comprising: providing a cell comprising a sample chamber; placing a boron-doped diamond electrode on an inner surface of the sample chamber; placing a removable stir bar in the sample chamber, the removable stir bar directly contacting and touching the boron-doped diamond electrode; and wherein the stir bar can be operated to rotate within the sample chamber upon the boron-doped diamond electrode.

Another embodiment provides a device for stirring a sample in a cell, comprising: a cell comprising a sample chamber; a boron-doped diamond electrode located on an inner surface of the sample chamber; a removable stir bar, placed in the sample chamber, directly contacting with and touching the boron-doped diamond electrode; and wherein the stir bar can be operated to rotate within the sample chamber upon the boron-doped diamond electrode.

A further embodiment provides a device for stirring a sample in a cell, comprising: a cell comprising a sample chamber, wherein the cell performs a coulometric measurement; a boron-doped diamond electrode located on an inner surface of the sample chamber; a removable stir bar, placed in the sample chamber, directly contacting the boron-doped diamond electrode, wherein the removable stir bar further comprises a magnet; a stir plate under the boron-doped electrode rotating a second magnet under the removeable stir bar to rotate the magnet of the stir bar; and wherein the stir bar can be operated to rotate within the sample chamber upon the boron-doped diamond electrode.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
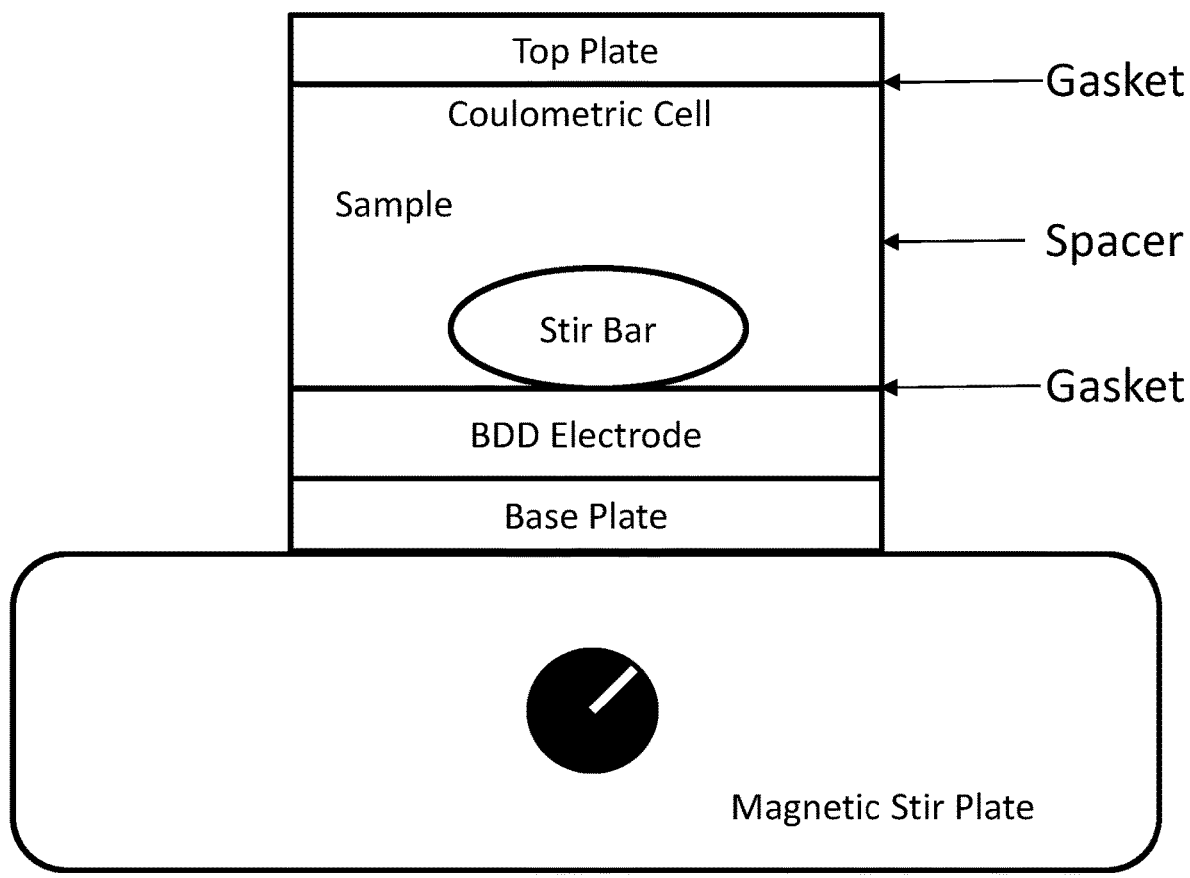
FIG. 1 illustrates an example diagram of a stir bar directly upon a boron-doped diamond electrode in a measurement cell.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

The measurement of the alkalinity of water or other aqueous solution or sample is very common and allows for determination of the quality of aqueous solutions. Typical water quality analysis tests for alkalinity are performed manually using time-consuming titrations. A conventional alkalinity measurement technique requires that a user manually add a strong acid to the aqueous sample to determine, by titration, the alkalinity of the sample. One technique requires a careful addition of sulfuric acid into a solution and the determination of an endpoint that can be correlated to the alkalinity of the sample. The end point is often a pH value. While some alkalinity measurement instruments for online monitoring or control are available, these instruments are often expensive and complex.

A coulometric alkalinity measurement system performs alkalinity measurements using an electrochemical cell. Such an alkalinity determination system may use electrochemical reactions for producing acid (i.e., protons) in situ, foregoing the need for an external titrant. These electrochemical methods may generate protons in situ through oxidation of water within the sample itself. In this system, the protons generated can be the titrant for determination of alkalinity of a water sample. For example, for the electrochemical oxidation of water, proton generation is generally proportional to the electron flow which may then be correlated to the amount of acid introduced to a sample. This controlled acid formation can be used in a coulometric titration for alkalinity. The generation of protons in situ from the sample eliminates the need for metering reagents such as acid delivery in a manual titration reaction. Thus, online electrochemical titration methods may be easier to use and do not require concentrated acid.

Conventional coulometric methods for titration of a sample for measurement of alkalinity frequently utilize a series of electrodes to perform the measurement. Such measurement systems include the use of a reference electrode, a counter (or auxiliary) electrode and a working electrode for production of protons via oxidation of water. Additionally, a pH sensing electrode is employed for monitoring the progress of the titration. Typically, the electrodes mentioned are placed in a sample to be measured from above with a stir bar sitting in the bottom of the sample container to homogenize the sample during the titration and provide a more accurate and rapid measurement. In general practice, the stirring component, for example a stir bar, is not intended to strike the electrodes used in the measurement for concerns of interference with the measurement or causing damage to the electrodes. The use of a stir bar directly contacting an electrode surface, for example, is not conventional. This may be especially true for conventional metallic electrodes, such as gold or platinum, which may be more easily scratched or damaged by contact with a moving element such as a stir bar. Moreover, as cell and sample volumes decrease, as is often desired in coulometric titrations, stirring becomes challenging if avoiding contact of stirring elements with electrodes in the sample.

In some electrochemical measurement systems, there are designs for having items impacting or scraping an electrode surface. This is often intended for reducing fouling buildup on a surface of an electrode or maintaining a fresh electrode surface, especially with the use of metallic electrodes such as gold or platinum. Conventional methods may use a grit, a ball (metal or plastic), or other physical object to abrade an electrode via random and intermittent strikes. However, electrodes composed of gold or platinum, for example, are susceptible to damage or wear from strikes by another object. Surface changes on an electrode may result in erroneous measurements. What is needed is a method to stir a sample during a coulometric titration that improves mixing of the sample, increases longevity of an electrode, and improves accuracy of a measurement.

Accordingly, the systems and methods described herein provide a method and device for stirring a sample. The sample may be measured using coulometric methods. The measurement may involve a titration. The titration may comprise the addition of protons which may be generated in situ or added as an acid. In an embodiment, a sample alkalinity may be measured using a pH electrode. In an embodiment, a boron-doped diamond (BDD) electrode may be used as an anode for oxidation of water to form protons in the sample. BDD electrodes are less susceptible to wear and damage due to impact by stirring and cleaning elements (such as beads or stir bars) than more conventional electrode materials such as gold or platinum and will therefore provide for a more stable and accurate measurement over time. In an embodiment, a stir bar may be placed directly upon the BDD electrode. The BDD electrode may form at least a portion of a bottom or wall of a cell or coulometric cell. The cell with the stir bar therein, and a BDD electrode forming at least a portion of the bottom or a wall of the cell or sample chamber may be placed upon a stir plate or magnetic stir plate. The stir plate may be a separate device or may be integrated into a unit with the cell. The stir plate may contain a motor or the like to rotate a magnet, which in turn, may rotate a magnet of the stir bar. The stir bar directly upon the BDD electrode may stir the sample, reduce fouling, clean the electrode surface, degas a sample, reduce bubbles, or the like. Such an arrangement is especially useful for a small sample volume, for example less than 1 milliliter (mL), in which stirring in needed for improved measurement performance.

The illustrated example embodiments will be best understood by reference to the figures. The following description is intended only by way of example, and simply illustrates certain example embodiments.

Referring to FIG. 1, in an embodiment, a sample may be stirred in a chamber or cell. The cell may be a coulometric cell. In an embodiment, the volume of the coulometric cell may be small. For example, the coulometric cell volume may be less than 1 milliliter (mL). The sample may be stirred during a coulometric titration. In an embodiment, the aqueous sample or sample may be oxidized. For example, water may be oxidized at an electrode. The oxidation of the water may generate protons. The proton generation may decrease the pH of the sample toward a more acidic condition. In an embodiment, a stirring or convection of the sample during the titration may increase the speed in which the titration may be performed. The stirring may increase the accuracy of a measurement of the sample during a coulometric titration.

In an embodiment, an electrode for oxidation of water may be a boron-doped diamond (BDD) electrode. In an embodiment, the BDD electrode may form at least a portion of the bottom or a wall of the cell in which a sample may be placed. The BDD electrode may be polished. The BDD electrode may be referred to as a protonator, or generator of protons. A stir bar or a removeable stir bar may be placed directly upon a surface of the BDD protonator electrode (See FIG. 1). The stir bar may be a magnetic stir bar. The stir bar may be removable from the cell or sample chamber. The stir bar may be constructed of an outer layer of a nonstick and/or chemically nonreactive matter. As an example, the stir bar may be 2 mm by 2 mm by 7 mm. However, the dimensions of the stir bar may be adjusted for a given cell size, sample composition, or another parameter. In an embodiment, the stir bar may contact the BDD electrode along the stir bar length to improve the anti-fouling of the BDD electrode. In an embodiment, the stir bar may have a "belt" to allow the stir bar to contact the BDD minimally to improve stirring but minimize contact with the BDD electrode, if desired.

In an embodiment, a stir bar may directly contact a surface of a BDD electrode, and that stir bar and BDD assembly may be associated with a stirring mechanism (See FIG. 1). The stirring mechanism may be a means for turning the stir bar. For example, the stir mechanism may have a magnet mechanically coupled to a drive motor or mechanism, which in turn, rotates the stir bar. A base plate, gasket, spacer, or the like may be between the BDD electrode and the stir plate. As an example, there may be a BDD electrode attached to a base plate, a gasket, a spacer, another gasket, and a top plate upon the stir plate. A gasket may be a material to seal surfaces against fluid transfer. A gasket may be a rubber, silicon, or the like material. A spacer may be plastic, metal, or the like and sized for a particular application. In an embodiment, an aperture may be formed by the base plate to allow an electrical connection to the BDD electrode. In another embodiment, the aperture for an electrical connection to the BDD electrode may be located in any portion of the stacked components between the BDD electrode and the stir plate. In an embodiment, the stirring and associated stirring motor may be pulsed or turned off during a measurement phase. In other words, if a measurement electrode in the cell receives electrical interference, sensitivity to vibration, or the like, the motor may be switched off during a measurement.

In an embodiment, a sample may be introduced and evacuated from the cell. The stirring may facilitate the movement of the sample during a measurement and/or for the introduction, flushing, and evacuation of the sample from the cell. The stirring may reduce the formation of bubbles during a flushing and/or measurement phase of the measurement. The stirring may aid in moving bubbles out of the sample cell. The stirring may move particulates within the cell or from the surface of the BDD electrode. The stirring may increase the movement or convection of the sample during a titration of the sample. In an embodiment, the sample may be cold, and a cold liquid may hold a greater amount of dissolved gas which can form bubbles. The stirring may reduce the bubbles trapped in a sample cell from a cold temperature sample.

In an embodiment, the stir bar is directly upon the surface of the BDD electrode. Other electrode material types, such as platinum, gold, and glassy carbon, may wear or be degraded by action of a stir bar stirring in direct contact with the electrode. Damage or deformation of the electrode of those type may affect the coulometric measurement over time, especially in the presence of abrasive particulates. BDD is a hard material and may allow for the use of a stir bar directly upon the diamond surface without imparting detrimental-to-performance wear or damage. The stir bar upon the BDD electrode may also reduce fouling or buildup of material upon the BDD electrode by performing as a wiping mechanism. This cleaning mechanism may reduce downtime, improve performance, and increase longevity of the BDD electrode. Also, the device and method demonstrate high reproducibility as the system does not rely on diffusion within the cell.

An embodiment may measure the alkalinity of a sample or an aqueous sample. Traditional approaches may use a titration of a sample for measurement of alkalinity. Acid may be added to a sample of known volume to titrate the sample's alkalinity. The pH of the sample may be measured with a pH sensor to monitor the change in sample pH with the addition of acid. An example of a pH sensor may be a glass pH electrode. Acid is added until the pH end point is reached for the titration. For example, acid is added until the sample pH is pH 4.5 for determination of Total Alkalinity. The total amount of acid added to a sample of known volume to reach the end point pH is used to determine the sample alkalinity. In a coulometric titration for determination of alkalinity, acid may be produced in situ by oxidation of water. In an embodiment, a BDD electrode may oxidize the water in a known volume of sample to produce protons and decrease the sample pH. The change in the sample pH may be monitored with a pH sensor. A glass pH electrode may be used to monitor pH. Other sensors for pH measurement may be ISFET, optical pH sensor, voltametric-based pH sensor, potentiometric metal oxide electrodes, and the like. The acid may be formed in situ in a sample until the endpoint pH is reached. The charge passed at the BDD electrode for production of protons to reach the titration endpoint may be correlated to the sample alkalinity.

In an embodiment, an aqueous sample may be introduced into a test chamber or coulometric cell. The aqueous sample may be placed or introduced into a test chamber manually by a user or using a mechanical means, for example, gravity flow, a pump, pressure, fluid flow, or the like. For example, a water sample for alkalinity testing may be introduced to a chamber by a pump. In an embodiment, there may be one or more chambers in which the one or more method steps may be performed. In an embodiment, valves or the like may control the influx and efflux of the aqueous solution into or out of the one or more chambers, if present. Once the sample is introduced to the measurement system, the system may measure the pH of the sample. This pH value may be used to determine whether the sample has a pH at or below the titration end point. For example, the pH value may indicate that the titration end point values may be between pH 4.5 and pH 4.3 or lower, indicating no alkalinity in the sample. Stirring of the sample improves pH measurement stabilization time and accuracy.

In an embodiment, the electrodes may be fully or at least partially disposed in the volume of aqueous solution. For example, if the aqueous solution is introduced into a chamber having one or more electrodes, the aqueous solution may at least partially cover the one or more electrodes. As another example, the one or more electrodes may be partially disposed within the chamber with the other portion of the electrode outside the chamber. Thus, when the aqueous solution is introduced into the chamber it only covers the portion of the electrodes that are within the chamber.

In an embodiment, the system may apply a voltage step waveform for proton generation. In an embodiment, the voltage step waveform may comprise one or more waves, pulses, potential pulses, or the like. In an embodiment, the voltage may be referred to as an electrical signal. The applied electrical signal may be any electrical signal selected from a waveform group, for example, a pulse, a step, a sawtooth, a sine wave, a square, a triangle, or the like or any combination thereof. Thus, the applied electrical signal may be applied as continuous pulses or intermittent electrical signals. Response optimization may be accomplished for a sample by selective choice of electrical signal amplitude and/or period. The electrical signal may be a preprogrammed waveform, may be altered during a measurement, and/or may be controlled by the system or by a user. The electrical signal may be applied using one or more electrodes, for example, a series of electrodes. Electrodes may include a working electrode, counter (auxiliary) electrode, reference electrode, or the like. In an embodiment, the one or more series of electrodes may be boron doped diamond (BDD) electrodes. Other electrode material are disclosed and contemplated. The use of BDD may serve as a better electrode material for oxidation of water and formation of protons than other carbon-based or metallic materials (e.g., silver, gold, mercury, nickel, glassy carbon, etc.) because these materials may eventually themselves become oxidized, thereby generating interfering signals and contributing to the errors in the measurement of alkalinity.

In an embodiment the method and system may titrate the aqueous sample. In an embodiment, protons may be added to the aqueous sample. For example, protons may be added using an acid, such as in a liquid form. Alternatively, proton may be generated in situ as in a coulometric titration. One or more electrodes may be designed to function at a potential to generate protons. The protonator electrode may hold at the applied potential to generate an amount of protons. Alternatively, a protonator electrode may hold a constant current for generation of protons at a set rate. The generation of protons may occur in a single process or by a series of proton formation steps. Stirring of the sample facilitates an optimized protonation step by homogenizing the sample during the titration process. The generated protons neutralize buffer capacity and facilitates the determination of alkalinity.

In an embodiment, the method and system may measure a current output. In an embodiment, the charge passed for the formation of protons may be correlated to the alkalinity of a sample. For example, the total charge passed at the protonator electrode to decrease the pH to the titration endpoint can be related to the sample alkalinity.

In an embodiment, the system may output an alkalinity of the aqueous sample. The alkalinity measurement may be based upon a comparison of the current observed for protonation of the sample and thereby, the acid added to the sample. In an embodiment, an alkalinity of a sample may be based upon a number of protons generated in an aqueous sample. For a coulometric titration, a number of protons generated may be correlated to a charge passed, a current passed or a time passed.

In an embodiment, an output may be in the form of a display, storing the data to a memory device, sending the output through a connected or wireless system, printing the output, or the like. The system may be automated, meaning the system may automatically output the electrode. The system may also have associated alarms, limits, or predetermined thresholds. For example, if a measured peak-to-peak separation reaches a threshold, the system may trigger an alarm, alert the system/personnel to a fault, alter the flow of the aqueous solution, or the like. Data may be analyzed in real-time, stored for later use, or any combination thereof.

The various embodiments described herein thus represent a technical improvement to conventional methods and instrument for alkalinity measurement. Using the techniques as described herein, an embodiment may use a method and device for an instrument for alkalinity measurement in a faster time frame. This is in contrast to conventional methods with limitations mentioned above. Such techniques provide a better method to construct and an instrument for alkalinity measurement.

Figure 2:
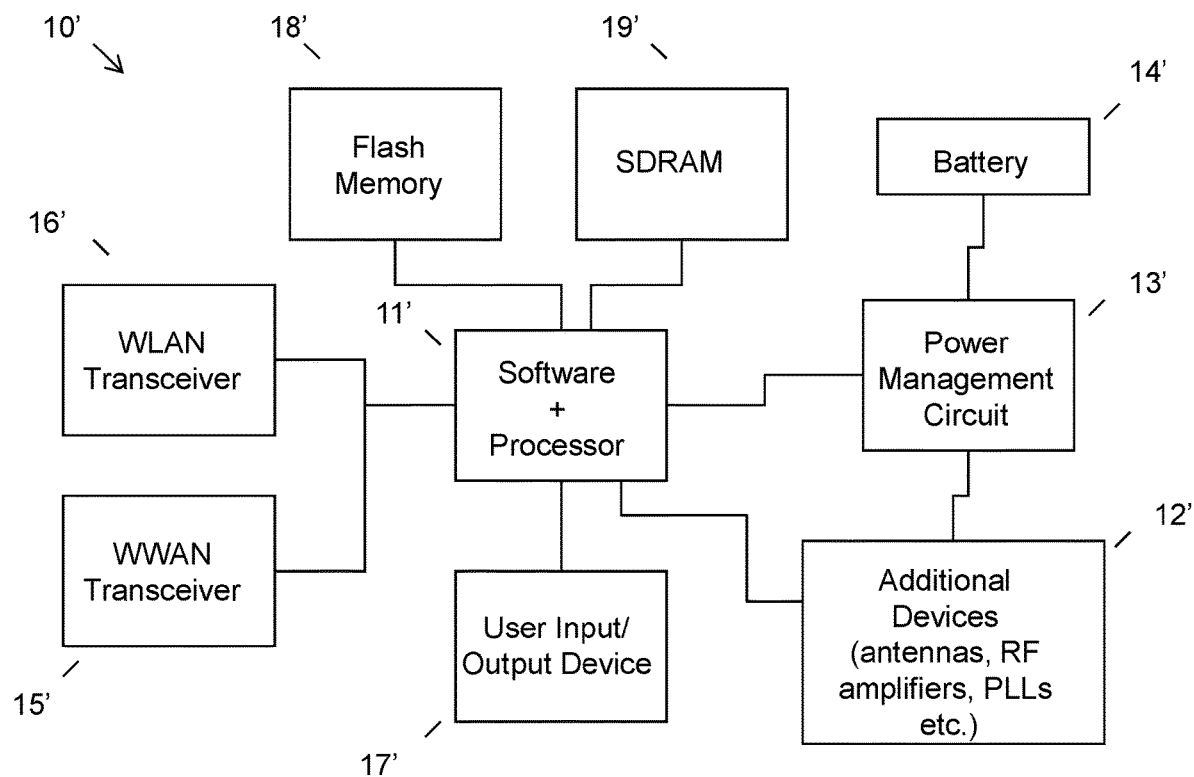
FIG. 2 illustrates an example of computer circuitry.

While various other circuits, circuitry or components may be utilized in information handling devices, with regard to an instrument for alkalinity measurement according to any one of the various embodiments described herein, an example is illustrated in FIG. 2. Device circuitry 10' may include a measurement system on a chip design found, for example, a particular computing platform (e.g., mobile computing, desktop computing, etc.) Software and processor (s) are combined in a single chip 11'. Processors comprise internal arithmetic units, registers, cache memory, busses, I/O ports, etc., as is well known in the art. Internal busses and the like depend on different vendors, but essentially all the peripheral devices (12') may attach to a single chip 11'. The circuitry 10' combines the processor, memory control, and I/O controller hub all into a single chip 11'. Also, systems 10' of this type do not typically use SATA or PCI or LPC. Common interfaces, for example, include SDIO and I2C.

There are power management chip(s) 13', e.g., a battery management unit, BMU, which manage power as supplied, for example, via a rechargeable battery 14', which may be recharged by a connection to a power source (not shown). In at least one design, a single chip, such as 11', is used to supply BIOS like functionality and DRAM memory.

System 10' typically includes one or more of a WWAN transceiver 15' and a WLAN transceiver 16' for connecting to various networks, such as telecommunications networks and wireless Internet devices, e.g., access points. Additionally, devices 12' are commonly included, e.g., a transmit and receive antenna, oscillators, PLLs, etc. System 10' includes input/output devices 17' for data input and display/rendering (e.g., a computing location located away from the single beam system that is easily accessible by a user). System 10' also typically includes various memory devices, for example flash memory 18' and SDRAM 19'.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment of an instrument for alkalinity measurement.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a measurement device such as illustrated in FIG. 1, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for stirring a sample in a cell, comprising:
   providing a cell comprising a sample chamber;
   placing a boron-doped diamond electrode on an inner surface of the sample chamber,
   placing a removable stir bar in the sample chamber, the removable stir bar directly contacting and touching the boron-doped diamond electrode; and
   wherein the stir bar can be operated to rotate within the sample chamber upon the boron-doped diamond electrode.

2. The method of claim 1, wherein the cell performs a coulometric measurement.

3. The method of claim 1, wherein the stir bar further comprises a magnet.

4. The method of claim 3, further comprising a stir plate under the boron-doped diamond electrode rotating a second magnet under the removeable stir bar to rotate the magnet of the stir bar.

5. The method of claim 1, wherein the removable stir bar mechanically wipes a surface of the boron-doped diamond electrode.

6. The method of claim 1, wherein the removable stir bar removes a fouling upon a surface of the boron-doped diamond electrode.

7. The method of claim 1, wherein the removable stir bar degases the sample.

8. The method of claim 1, further comprising a base plate located between the boron-doped diamond electrode and a stir plate.

9. The method of claim 8, further comprising a first gasket between the boron-doped diamond electrode and a spacer and a second gasket between the spacer and a top plate.

10. The method of claim 1, wherein the sample is a water sample for titration.

11. A device for stirring a sample in a cell, comprising:
    a cell comprising a sample chamber;
    a boron-doped diamond electrode located on an inner surface of the sample chamber;
    a removable stir bar, placed in the sample chamber, directly contacting with and touching the boron-doped diamond electrode; and
    wherein the stir bar can be operated to rotate within the sample chamber upon the boron-doped diamond electrode.

12. The device of claim 11, wherein the cell performs a coulometric measurement.

13. The device of claim 11, wherein the stir bar further comprises a magnet.

14. The device of claim 13, further comprising a stir plate under the boron-doped diamond electrode rotating a second magnet under the removeable stir bar to rotate the magnet of the stir bar.

15. The device of claim 11, wherein the removable stir bar mechanically wipes a surface of the boron-doped diamond electrode.

16. The device of claim 11, wherein the removable stir bar removes a fouling upon a surface of the boron-doped diamond electrode.

17. The device of claim 11, wherein the removable stir bar degases the sample.

18. The device of claim 11, further comprising a base plate located between the boron-doped diamond electrode and a stir plate.

19. The device of claim 18, further comprising a first gasket between the boron-doped diamond electrode and a spacer and a second gasket between the spacer and a top plate.

20. A device for stirring a sample in a cell, comprising:
    a cell comprising a sample chamber, wherein the cell performs a coulometric measurement;
    a boron-doped diamond electrode located on an inner surface of the sample chamber;
    a removable stir bar, placed in the sample chamber, directly contacting the boron-doped diamond electrode, wherein the removable stir bar further comprises a magnet;
    a stir plate under the boron-doped electrode rotating a second magnet under the removeable stir bar to rotate the magnet of the stir bar; and
    wherein the stir bar can be operated to rotate within the sample chamber upon the boron-doped diamond electrode.

* * * * *